US008858981B2

(12) United States Patent
Geistlich

(10) Patent No.: US 8,858,981 B2

(45) Date of Patent: Oct. 14, 2014

(54) BONE HEALING MATERIAL COMPRISING MATRIX CARRYING BONE-FORMING CELLS

(75) Inventor: Peter Geistlich, Stansstad (CH)

(73) Assignee: Ed. Geistlich Soehne Fuer Chemistrie Industrie, Wolhusen (CH)

(*) Notice: Subject to any disclaimer, the term of this patent is extended or adjusted under 35 U.S.C. 154(b) by 613 days.

(21) Appl. No.: 11/317,247

(22) Filed: Dec. 27, 2005

(65) Prior Publication Data

US 2006/0159668 A1 Jul. 20, 2006

Related U.S. Application Data

(63) Continuation-in-part of application No. 10/367,979, filed on Feb. 19, 2003, now abandoned, and a continuation-in-part of application No. 11/046,897, filed on Feb. 1, 2005, now abandoned, which is a continuation-in-part of application No. 10/213,437, filed on Aug. 7, 2002, now abandoned, said application No. 11/046,897 is a continuation-in-part of application No. 09/925,728, filed on Aug. 10, 2001, now Pat. No. 7,141,072, and a continuation-in-part of application No. 09/545,465, filed on Apr. 7, 2000, now Pat. No. 6,752,834, said application No. 11/046,897 is a continuation-in-part of application No. 10/869,909, filed on Jun. 18, 2004, now abandoned, which is a continuation of application No. 09/545,465, filed on Apr. 7, 2000, now Pat. No. 6,752,834, which is a continuation-in-part of application No. PCT/GB98/02976, filed on Oct. 5, 1998.

(60) Provisional application No. 60/357,839, filed on Feb. 21, 2002, provisional application No. 60/224,010, filed on Aug. 10, 2000.

(51) Int. Cl.

| | |
|---|---|
| ***A61F 2/28*** | (2006.01) |
| ***C12N 5/07*** | (2010.01) |
| ***C12N 11/02*** | (2006.01) |
| ***A61L 27/38*** | (2006.01) |
| ***A61L 27/24*** | (2006.01) |
| ***A61L 27/20*** | (2006.01) |

(52) U.S. Cl.

CPC ............. *A61L 27/20* (2013.01); *A61L 2430/06* (2013.01); *A61L 27/3847* (2013.01); *A61L 27/24* (2013.01); *A64L 2430/02* (2013.01); *A61L 27/3821* (2013.01)

USPC ........................... 424/426; 424/93.7; 435/177

(58) Field of Classification Search

None

See application file for complete search history.

(56) References Cited

U.S. PATENT DOCUMENTS

| | | | | |
|---|---|---|---|---|
| 4,394,370 | A | 7/1983 | Jefferies | |
| 4,488,911 | A | 12/1984 | Luck et al. | |
| 4,505,266 | A | 3/1985 | Yannas et al. | |
| 4,516,276 | A | 5/1985 | Mittelmeier et al. | |
| 4,880,429 | A | 11/1989 | Stone | |
| 4,975,527 | A | 12/1990 | Koezuka et al. | |
| 5,162,430 | A | 11/1992 | Rhee et al. | |
| 5,167,961 | A | 12/1992 | Lussi et al. | |
| 5,197,985 | A | 3/1993 | Caplan et al. | |
| 5,206,023 | A | 4/1993 | Hunziker | |
| 5,254,133 | A | 10/1993 | Seid | |
| 5,306,302 | A | 4/1994 | Bauer et al. | |
| 5,306,311 | A | 4/1994 | Stone et al. | |
| 5,413,597 | A | 5/1995 | Krajicek | |
| 5,417,975 | A | 5/1995 | Lussi et al. | |
| 5,523,348 | A | 6/1996 | Rhee et al. | |
| 5,541,295 | A | 7/1996 | Barrach et al. | |
| 5,567,806 | A | 10/1996 | Abdul-Malak et al. | |
| 5,573,771 | A | 11/1996 | Geistlich et al. | |
| 5,624,463 | A | 4/1997 | Stone et al. | |
| 5,759,190 | A | 6/1998 | Vibe-Hanson et al. | |
| 5,763,416 | A | 6/1998 | Bonadio et al. | |
| 5,837,278 | A * | 11/1998 | Geistlich et al. | 424/444 |
| 5,842,477 | A | 12/1998 | Naughton et al. | |
| 5,899,939 | A | 5/1999 | Boyce et al. | |
| 5,942,496 | A | 8/1999 | Bonadio et al. | |
| 5,989,269 | A | 11/1999 | Vibe-Hanson et al. | |
| 6,120,514 | A | 9/2000 | Vibe-Hansen et al. | |
| 6,153,292 | A | 11/2000 | Bell et al. | |
| 6,165,785 | A | 12/2000 | Ogle et al. | |
| 6,221,109 | B1 | 4/2001 | Geistlich et al. | |

(Continued)

FOREIGN PATENT DOCUMENTS

| | | |
|---|---|---|
| AU | 660045 | 6/1995 |
| AU | 663150 | 9/1995 |

(Continued)

OTHER PUBLICATIONS

Mason, JM, et al., Viral vector laboratory, NSUH, Manhasset, NY, (CORR, Nov. 2000), 7 pages.

H.A. Breinan et al., "Reparative Tissues in Articular Cartilage Defects in a Canne Model Treated by Microfracture", 45th Annual Meeting, Orthopaedic Research Society, Feb. 1-4, 1999, Anaheim, CA. (one page ).

C.R. Lee et al., "Harvest and Selected Cartilage Repair Procedures Affect Mechanical and Biochemical Properties of Uninvolved Articular Cartilage in the Canine Knee", 45th Annual Meeting, Orthopaedic Research Society, Feb. 1-4, 1999, Anaheim, CA. (one page).

(Continued)

*Primary Examiner* — David M Naff

(74) *Attorney, Agent, or Firm* — Rothwell, Figg, Ernst & Manbeck, P.C.

(57) ABSTRACT

A bone healing combination material includes a matrix carrying cultivated bone-forming cells which may be osteocytes, osteoblasts, stromal stem cells or stem cells committed to differentiation into bone-forming osteoblasts. The matrix is a purified collagen matrix material derived from natural collagen-containing animal tissue, a collagen-free porous bone mineral matrix material derived from natural bone having a crystal structure substantially that of natural bone and being substantially free from endogenous organic material, or a combination of purified collagen matrix material and porous bone mineral matrix material.

11 Claims, 3 Drawing Sheets

(56) References Cited

U.S. PATENT DOCUMENTS

| | | | |
|---|---|---|---|
| 6,283,980 | B1 | 9/2001 | Vibe-Hansen et al. |
| 6,352,558 | B1 | 3/2002 | Spector |
| 6,576,015 | B2 | 6/2003 | Geistlich et al. |
| 6,676,969 | B2 | 1/2004 | Geistlich et al. |
| 6,752,834 | B2 | 6/2004 | Geistlich et al. |
| 6,863,900 | B2 | 3/2005 | Kadiyala et al. |
| 2001/0016772 | A1 | 8/2001 | Lee et al. |
| 2002/0013626 | A1 | 1/2002 | Geistlich et al. |

FOREIGN PATENT DOCUMENTS

| | | | |
|---|---|---|---|
| CA | 2248327 | | 9/1997 |
| DE | 38 10803 | A1 | 10/1989 |
| DE | 196 54 884 | A | 9/1997 |
| DE | 196 54 884 | A1 | 9/1997 |
| EP | 0171176 | A2 | 2/1986 |
| JP | 2033388 | | 2/1990 |
| JP | 4-501070 | A | 2/1992 |
| JP | 4-226669 | A | 8/1992 |
| JP | 8-510984 | A | 11/1996 |
| JP | 2001-333974 | | 4/2001 |
| PL | 191497 | B1 | 1/2001 |
| WO | WO 83/04177 | A1 | 12/1983 |
| WO | WO 86/07265 | | 12/1986 |
| WO | 90/01955 | A1 | 3/1990 |
| WO | WO 90/05755 | A1 | 5/1990 |
| WO | WO 90/13302 | A1 | 11/1990 |
| WO | WO 92/13565 | A1 | 8/1992 |
| WO | WO 93/10722 | A2 | 6/1993 |
| WO | WO 93/11723 | A1 | 6/1993 |
| WO | WO 93/19168 | A1 | 9/1993 |
| WO | 94/21556 | A1 | 9/1994 |
| WO | WO 95/18638 | A1 | 7/1995 |
| WO | WO 96/24310 | A1 | 8/1996 |
| WO | WO 96/25961 | A1 | 8/1996 |
| WO | WO 97/32616 | A1 | 9/1997 |
| WO | 9738729 | A1 | 10/1997 |
| WO | WO 98/02976 | A1 | 1/1998 |
| WO | WO 98/08469 | A2 | 3/1998 |
| WO | WO 99/11664 | A1 | 3/1999 |
| WO | 9919005 | A1 | 4/1999 |
| WO | WO 99/19005 | A1 | 4/1999 |
| WO | WO 00/74741 | | 12/2000 |
| WO | WO 01/08714 | A1 | 2/2001 |
| WO | WO 01/15711 | A1 | 3/2001 |
| WO | WO 01/24842 | A2 | 4/2001 |
| WO | WO 0180714 | A2 | 11/2001 |
| WO | WO 01/91816 | A1 | 12/2001 |
| WO | WO 0124842 | A2 | 12/2001 |

OTHER PUBLICATIONS

C.R. Lee et al., "The Contractile Behavior of Articular Chondrocytes in Collagen Matrices in Vitro" , Tissue Engineering Soc., Dec. 4-6, 1998, Orlando, Fla. (one page).

S.M. Mueller et al., "Alpha-Smooth Muscle Actin in Bovine Meniscus Cells Seeded in Type I and Type II Collagen-Gag Matrices", 44th Annual Meeting, Orthopaedic Research Society, Mar. 16-19, 1998, New Orleans, Louisiana. (one page).

S. Nehrer et al., "Chondrocyte-Seeded Type I and Type II Collagen Implants Investigated in Vitro", Fifth World Biomaterials Congress, May 29-Jun. 2, 1996, Toronto, CA. (one page).

S. Nehrer et al., "Autologous Chondrocyte-Seeded Type I and II Collagen Matrices Implanted in a Chondral Defect In a Canine Model", 44th Annual Meeting, Orthopaedic Research Society, Mar. 16-19, 1998, New Orleans, Louisiana. (one page).

S. Nehrer et al., "Chondrocyte-Seeded Type I and Type II Collagen Matrices Implanted in a Chondral Defect in a Canine Model", 7th Conference European Orthopaedic Research Society, Barcelona, 1997. (one page).

S. Nehrer et al., "Characteristics of Articular Chondrocytes Seeded in Collagen Matrices in Vitro", Tissue Engineering, 1998, pp. 175-183, vol. 4(2).

S. Nehrer et al., "Matrix Collagen Type and Pore Size Influence Behaviour of Seeded Canine Chondrocytes", Biomaterials 18, (1997), pp. 769-776.

Donna Schulz-Torres et al., "Tendon Cell Contraction of Collagen-Gag Matrices in Vitro: Effect of Cross-Linking", Soc. For Biomaterials, Apr. 28-May 2, 1999, Providence, R.I. (one page).

S. Nehrer et al., "Canine Chondrocytes Seeded in Type I and Type II Collagen Implants Investigated in Vitro", J. Biomed. Mater. Res. (Appl. Biomater.), 1997, pp. 95-104, vol. 38, John Wiley & Sons, Inc.

"Carticel (Autologous cultured chondrocytes): Get in the Game", *Genzyme Tissue Repair*, 9 pp., 1998.

Menard, C., et al., "Contractile behavior of smooth muscle actin-containing osteoblasts in collagen-GAG matrices in vitro: implant-related cell contraction", *Biomaterials*, 21 (2000) 1867-1877.

Database WPI, 002241043, Derwent Publications Ltd., Jul. 26, 1990.

Database WPI, 002241044, Derwent Publications Ltd., Dec. 4, 2001.

Database Biosis, 002242287, "Lapine and canine bone marrow stromal cells contain smooth muscle actin and contract a collagen-slycoasminoglycan matrix", Dec. 2001.

Pieper, J.S., et al., "Development of Tailor-made Collagen-glycosaminoglycan Matrices: EDC/NHS Crosslinking, and Ultrastructural Aspects", *Biomaterials*, vol. 21, pp. 581-593 (2000).

Stone, K., et al., "Regeneration of Meniscal Cartilage with Use of a Collagen Scaffold", *The Journal of Bone and Joint Surgery, Incorporated*, vol. 79-A, No. 12, 1997, pp. 1770-1777.

S.M. Mueller et al., "α-Smooth Muscle Actin and Contractile Behavior of Bovine Meniscus Cells Seeded in Type I and Type II Collagen-GAG Matrices", J. Biomed. Mat. Res., 1999, pp. 1-10, vol. 45, John Wiley & Sons, Inc.

Genzyme Tissue Repair, "Carticel™ (autologous cultured chondrocytes), Engineering a Better Repair", Genzyme Tissue Repair, 64 Sidney Street, Cambridge, MA 02139-4136, Sep. 1997, brochure. (8 pages).

D. Mutter et al., "Biomaterial Supports for Colonic Wall Defect Healing", Biomaterials 17, 1996, pp. 1411-1415.

Schneider et al., "Expression of α-Smooth Muscle Actin in Canine Intervertebral Disc Cells in Situ and in Collagen-Glycosaminoglycan Matrices in Vitro", *J. Orthoped. Res.* 17(2): 192-199, 1999.

International Search Report, Oct. 13, 2008.

"Filler for defective bones or bone cavities—comprising spongy porous material of calcium phosphate cpds. Having three-dimensional continuous pores adhered with collagen", Derwent, Jan. 1, 1900. XP-002241043, 1pg.

Bio-Gide: Resorbable Bilayer Membrane for Bone Regeneration, Geistlich Biomaterials, 2 pp.

Chondro-Gide: Collagen Membrane for Articular Cartilage Repair, Geistlich Biomaterials, 15 pages.

Office Action issued in Japanese Patent Appln. No. 2009-264245 on Dec. 25, 2012 along with English translation, 4 pages.

K. Anselme et al.: "Association of porous hydroxyapatite and bone marrow cells for bone regeneration," Bone, 25(2 Suppl):51S-54S, Aug. 1999, Abstract Only.

M. Jafarian et al.: "Marrow-derived mesenchymal stem cells-directed bone regeneration in the dog mandible: a comparison between biphasic calcium phosphate and natural bone mineral," Oral Surg Oral Med Oral Pathol Oral Radiol Endod, 105:e14-e24, 2008, Abstract Only.

R. Gutwald et al.: "Mesenchymal stem cells and inorganic bovine bone mineral in sinus augmentation: comparison with augmentation by autologous bone in adult sheep," British Journal of Oral and Maxillofacial Surgery, vol. 48, Issue 4, pp. 285-290, Jun. 2010, Abstract Only.

Cai, et al., "Lapine and Canine Bone Marrow Stromal Cells Contain Smooth Muscle Actin and Contract a Collagen-Glycosaminoglycan Matrix," Tissue Engineering vol. 7(6):829-841, 2001.

* cited by examiner

BONE HEALING MATERIAL COMPRISING MATRIX CARRYING BONE-FORMING CELLS

CROSS-REFERENCE TO RELATED APPLICATIONS

This application is a continuation-in-part of U.S. application Ser. No. 10/367,979, filed Feb. 19, 2003, now abandoned, which claims benefit of U.S. Provisional Application No. 60/357,839, filed Feb. 21, 2002. The present application also is a continuation-in-part of U.S. application Ser. No. 11/046,897, filed Feb. 1, 2005, now abandoned, which is a continuation-in-part of U.S. application Ser. No. 10/213,437, filed Aug. 7, 2002, now abandoned, which claims the benefit of U.S. Provisional Application Ser. No. 60/311,078, filed Aug. 10, 2001. U.S. application Ser. No. 11/046,897 also is a continuation-in-part of U.S. application Ser. No. 09/925,728, filed Aug. 10, 2001, now U.S. Pat. No. 7,141,072, which claims the benefit of U.S. Provisional Application Ser. No. 60/224,010 filed Aug. 10, 2000. U.S. application Ser. No. 09/925,728 also is a continuation-in-part of U.S. application Ser. No. 09/545,465, filed Apr. 7, 2000, now U.S. Pat. No. 6,752,834 U.S. application Ser. No. 11/046,897, also is a continuation-in-part of U.S. application Ser. No. 10/869,909, filed Jun. 18, 2004, now abandoned, which is a continuation of U.S. application Ser. No. 09/545,465, filed Apr. 7, 2000. U.S. application Ser. No. 09/545,465 is a continuation-in-part of International Application Serial No. PCT/GB98/02976, filed Oct. 5, 1998.

FIELD OF THE INVENTION

The present invention relates to the field of reconstruction of bone tissue.

DESCRIPTION OF THE BACKGROUND ART

There remains a need in the art for materials and methods for promoting regeneration and reconstruction of bone tissue such as in the maxilla and other skeletal bone loss defects.

SUMMARY OF THE INVENTION

In accordance with the present invention, a bone healing combination material comprises a matrix carrying bone-forming cells selected from the group consisting of osteocytes, osteoblasts, stromal stem cells (e.g., present in bone marrow) and stem cells committed to differentiation into bone-forming osteoblasts. The matrix utilized in the present invention is selected from the group consisting of a purified collagen matrix material derived from natural collagen-containing animal tissue, a porous bone mineral matrix material derived from natural bone having a crystal structure substantially that of natural bone and being substantially free from endogenous organic substances or material, and a combination of said purified collagen matrix material and said porous bone mineral matrix material.

DETAILED DESCRIPTION OF THE INVENTION

As noted above, a matrix material for utilization in accordance with the present invention may be a collagen matrix material, a porous bone mineral matrix material or a combination thereof.

Figure 1:
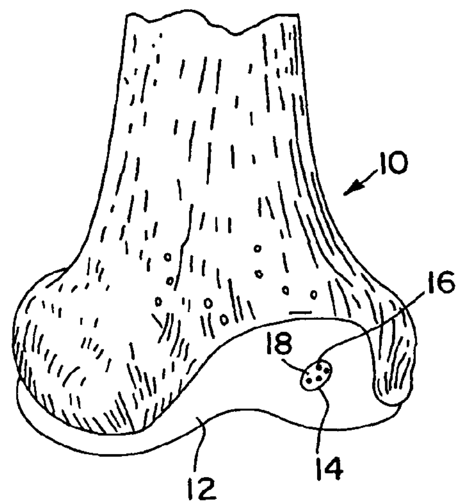
FIG. 1 is a schematic elevation view of a porous bone mineral matrix carrying bone-forming cells in accordance with one embodiment of the invention.

FIG. 1 shows a porous bone mineral matrix material 10 carrying bone-forming cells 12 in accordance with one embodiment of the invention. The porous bone mineral matrix 10 is described in more detail below, and, in accordance with one embodiment, is optionally charged or impregnated with a collagen material 14.

Figure 2:
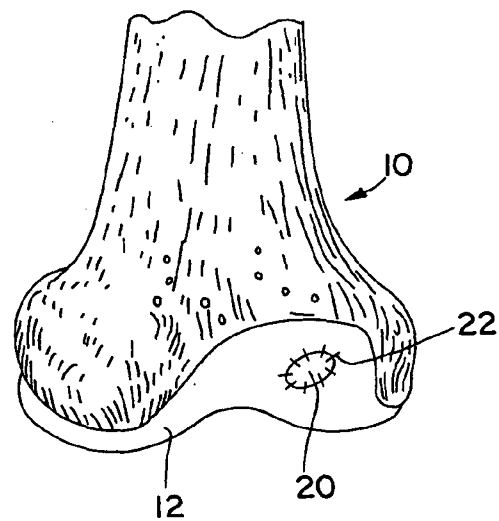
FIG. 2 is a schematic view in partial cross section of an area of bone loss being treated in accordance with the present invention.

FIG. 2 shows a bone loss defect 16 in bone 18 which may be in the maxilla, or other skeletal bone. In the embodiment shown in FIG. 2, porous bone mineral matrix material 10, which carries bone-forming cells in accordance with the present invention, is packed into the bone defect 16. The bone mineral matrix packing 10 may be held in place by a membrane 20 by any suitable means, such as fasteners 22. In certain embodiments, membrane 20 is a collagen matrix carrying bone-forming cells in accordance with the present invention. In another embodiment, the bone defect is covered with a collagen matrix 20 carrying bone-forming cells in accordance with the present invention, without the addition of bone mineral matrix 10.

Figure 3:
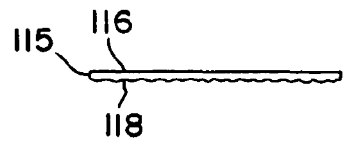
FIG. 3 is a side elevation schematic view showing a single-layer collagen matrix carrying bone-forming cells according to one embodiment of the invention.

In accordance with one embodiment, the collagen matrix material is a collagen membrane material comprised of at least one barrier layer having at least one smooth face so as to inhibit cell adhesion thereon and act as a barrier to prevent passage of cells therethrough. The barrier layer further has a fibrous face opposite the smooth face, the fibrous face allowing cell growth thereon. The smooth face preferably is oriented away from the area to be treated, and the fibrous face preferably is oriented toward the area to be treated. In preferred embodiments, the barrier layer is predominantly collagen I, collagen III or a mixture thereof. One suitable material is Biogide® from Ed. Geistlich Soehne AG fur Chemische Industrie, the assignee of the present invention. The Biogide® material is described in U.S. Pat. No. 5,837,278, incorporated herein by reference. The Biogide® may be derived from pig peritoneum. The material shown in FIG. 3 is comprised of at least one barrier layer 115 having at least one smooth face 116 so as to inhibit cell adhesion thereon and act as a barrier to prevent passage of cells therethrough. The barrier layer 115 further has a fibrous face 118.

Figure 4:
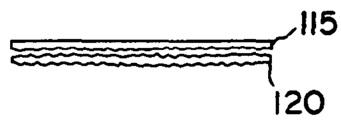
FIG. 4 is a side elevation schematic view showing a double-layer matrix carrying bone-forming cells according to another embodiment of the present invention.
Figure 4A:
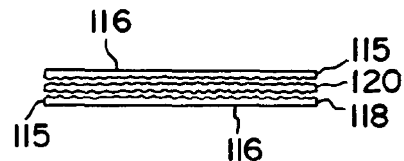

A multi-layer membrane which may be used in accordance with the present invention includes a barrier layer, and further includes a matrix layer predominantly of collagen II having an open sponge-like texture. Such a collagen membrane is described in PCT Application No. PCT/GB98/02976, U.S. Ser. No. 09/545,465, filed Apr. 7, 2000, claiming priority from U.K. patent application no. 9721585.9, filed Oct. 10, 1997, incorporated herein by reference. This membrane includes a barrier layer 115 as shown in FIG. 4, and further includes a matrix layer 120 predominantly of collagen II having an open sponge-light texture.

Figure 5:
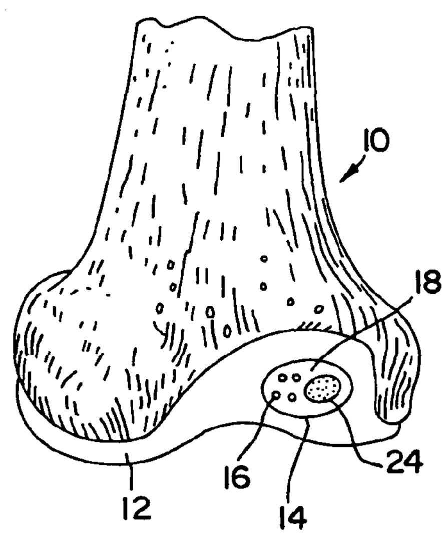
FIG. 5 is a side elevation schematic view showing a triple-layer matrix carrying bone-forming cells in accordance with a further embodiment of the present invention.

Another multi-layer membrane which may be used in accordance with the present invention includes a pair of barrier layers sandwiched around a central matrix layer predominately of collagen II having an open sponge-like texture. In accordance with this embodiment, smooth faces of the barrier layers are oriented outwardly, and fibrous faces of barrier layers are oriented inwardly toward the matrix layer. This membrane includes two barrier layers 115, each having outwardly oriented smooth faces 116, with a collagen II matrix layer 120 sandwiched therebetween, as shown in FIG. 5.

Figure 6:
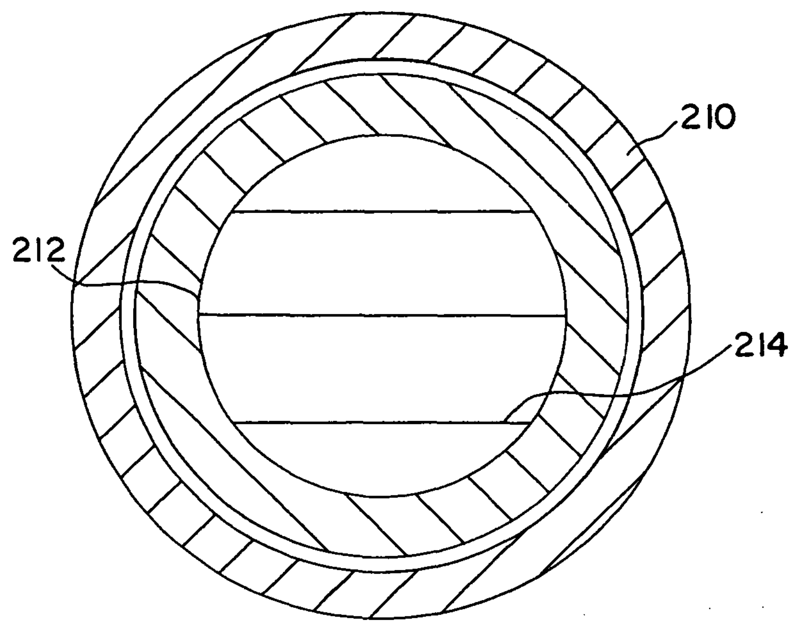
FIG. 6 is a side elevation schematic view showing a single-layer matrix carrying bone-forming cells according to still another embodiment of the invention.

FIG. 6 shows another embodiment in which a single collagen II matrix layer 120 carries bone-forming cells in accordance with the present invention.

Collagen occurs in a number of forms in the animal body and different tissues contain different proportions of the respective types. Bone collagen comprises predominantly collagen I and III. Cartilage comprises predominantly collagen II together with small quantities of collagen VI, IX, X, XI and XIII. Collagen material derived from skin and tendons is mostly made up of collagen I and/or III.

According to one aspect of the present invention, therefore, there is provided a resorbable extracellular matrix for reconstruction of cartilage tissue comprising predominantly fibres of collagen II.

A collagen II matrix according to the invention may contain minor quantities of collagen VI, IX, X, XI and XIII. The matrix according to the invention may also contain a hydrogel-like material, for example comprising glycosaminoglycans such as chondroitin sulphate, keratan sulphate, dermatan sulphate and hyaluronic acid, which provides a natural medium in which chondrocytes can become embedded and grow. The matrix according to the invention may contain 0.1 to 40% by weight of glycosaminoglycan, for example 1-15%, e.g., about 2-3 by weight, most preferably about 2.5% by weight.

A matrix according to the invention may either comprise natural cartilage material which has been subjected to defatting and other treatment, leaving the collagen material together with glycosaminoglycans, or alternatively fibres of purified collagen may be mixed with glycosaminoglycans and/or any other additives. Such additional additives may, for example, include chondronectin or anchorin II to assist attachment of the chondrocytes to the collagen fibres and growth factors such as cartilage inducing factor (CIF), insulin-like growth factor (IGF) and transforming growth factor β (TGFβ).

To aid in regenerating bone tissue, the matrix is impregnated with osteocytes, osteoblasts, stromal stem cells (e.g., present in bone marrow) or osteoblast-forming stem cells, either prior to or following implantation in vivo. While the matrix may be impregnated with the cells immediately prior to implantation, e.g. by injection, it is expected that in general the cells will be introduced into the matrix by direct injection of a suspension of cells following implantation. In this way, the cells present in the matrix are able to effect regeneration of new bone.

Osteocytes, osteoblasts or osteoblast-forming stem cells for use in the invention may be obtained from cell sources which include allogenic or autogenic cells isolated from tissue containing osteoblasts or osteoblast-forming stem cells. Since allogenic cells carry the potential for immune response and infectious complications, it is preferable to isolate the osteoblasts or osteoblast-forming stem cells from autogenic cells. Techniques for harvesting cells are known and include enzymatic digestion or outgrowth culture. The harvested cells are then expanded in cell culture prior to reintroduction to the body. In general, at least 106, preferably at least 107 cells should be impregnated into the matrix to provide for optimal regeneration of bone tissue.

Alternatively, bone marrow or bone marrow derivative containing stromal stem cells can be charged into the matrix.

In general, it is desirable for the matrix according to the invention to contain glycosaminoglycans (GAGs) such as hyaluronic acid, chondroitin 6-sulphate, keratin sulphate, dermatan sulphate, etc., which serve to provide a natural medium in which osteoblasts or osteoblast-forming stem cells can become embedded and grow. While it is possible to incorporate into the matrix glycosaminoglycans from different sources which do not necessarily have the same composition, molecular weight and physiological properties as those from cartilage, preferred glycosaminoglycans are those extracted from cartilage itself.

In native collagen tissues GAGs occur, at least in part, as a component of proteoglycans (PGs). The use of GAGs in the form of PGs is undesirable in view of potential immunological problems which can be caused by the protein content of the PGs. Preferably, the matrix is thus substantially free from any proteoglycans. Conveniently, this may be achieved by preparing the matrix from a mixture of a purified telopeptide-free collagen material and glycosaminoglycans.

Other additives which may also be present in the matrix include, for example, chondronectin, laminin, fibronectin, calcium alginate or anchorin II to assist attachment of the chondrocytes to the collagen II fibers, bone and cartilage cell growth-promoting hormones, and growth factors such as cartilage inducing factor (CIP), insulin-like growth factor (IGF), transforming growth factor β (TGFβ) present as homodimers or heterodimers, osteogenic protein-1 (OP-1) and bone morphogenetic factors (BMPs) such as native or recombinant human BMP-2, BMP-3 (osteogenin), BMP-4, BMP-7, BMP-8, bFGF, CDMP or other skeletal matrix molecules, as well as signaling peptides such as transforming growth factor-β (TGF-β, TGF-β1), vascular endothelial growth factor (EGF/VEGF), insulin-like growth factor (IGF/IGF-1), parathyroid hormone related protein (PTHrP) and platelet derived growth factor (PDGF). Nucleic acid sequences coding for the above, or which are capable of inducing or promoting in vivo production of the above, may be incorporated into the matrix material of the present invention.

As noted above, the product used in the invention also may act as a carrier for stem cells committed to differentiation into bone-producing cells. Such stem cells may be grown in vitro to increase their numbers, and applied to the repair sites in the carrier matrices with or without growth factors. An example is bone marrow stromal cells. Nucleic acid sequences coding for the above, or which are capable of inducing or promoting in vivo production of the above, may be incorporated into the matrix material of the present invention.

BMP-2 affects the two pathways of bone formation independently—the direct formation of bone as well as the formation of cartilage which is then removed and replaced by bone. Composites of BMPs and collagen including bone matrix obtained by extraction from cortical bone from various sources or demineralized bone matrix comprise about 90% collagen and about 10% non-collagenous proteins (NCP) for BMP activity or for BMP/NCP induced chondrogenesis. Bone matrix-insoluble collagenous matrix and laminin or fibronectin act as carriers for BMPs. In general, the matrix may contain from about 100 μg to about 5 mg of growth factors. Nucleic acid sequences coding for the above, or which are capable of inducing or promoting in vivo production of the above, may be incorporated into the matrix material of the present invention.

A matrix material for use in accordance with the present invention may also be charged with parathyroid hormone (PTH), a polypeptide involved in regulation of calcium in the body. Nucleic acid sequences coding for the above, or which are capable of inducing or promoting in vivo production of the above, may be incorporated into the matrix material of the present invention.

As noted above, the present invention may comprise a gene or nucleic acid-supplemented matrix with cell growth-promoting genetic material or DNA incorporated therein. The matrix material may provide for prolonged release of the cell growth-promoting genetic material. Upon release from the matrix into the body, the genetic material may transform cells in the body so as to promote cell growth and healing.

The present invention may also provide a matrix material charged with a cell growth-promoting nucleic acid sequence, preferably an isolated or purified nucleic acid sequence. The sequence can be a DNA sequence or an RNA sequence. In particularly preferred embodiments, the matrix material is charged with an isolated gene sequence, most preferably of DNA.

A nucleic acid sequence for use in accordance with the present invention may promote cartilage cell growth, bone cell growth, or both.

Purified therapeutic nucleic acid sequences for use in accordance with the present invention may be derived from any suitable source, and may be charged to the matrix material so as to promote cell growth. In accordance with one embodiment, a retroviral vector, or any other suitable gene-carrying and gene-introducing mechanism, is utilized. For example, a retroviral vector may be utilized for stably introducing human bone morphogenic protein 7 (BMP-7) cDNA into mesenchymal stem cells.

Gene therapy involves the delivery of therapeutic genes or other genetic material into cells and tissues.

As will be further discussed below, a collagen matrix of the invention may be prepared by forming an aqueous collagen slurry, optional partial dehydration of the slurry, molding the slurry to the desired shape, drying of the slurry, partial cross-linking of the collagen fibers by chemical, ultraviolet (UV) radiation or hydrothermal cross-linking, and sterilizing the implant material. Alternatively, cross-linking, such as chemical cross-linking, can be effected after preparation of the slurry and prior to molding.

In preferred embodiments, the molded material is dried by freeze-drying so as to achieve a pore size within the range of about 0.1-500 μm. A preferred pore size for a matrix in accordance with the invention is within the range of about 50-400 μm, most preferably within the range of about 70-120 μm.

The density of the matrix after freeze-drying preferably is within the range of about 0.1-0.3 g/m$^3$, preferably about 0.18-0.22 g/m$^3$, most preferably about 0.2 g/m$^3$.

Collagen material may be cross-linked before or after the freeze-drying step to stabilize the matrix. This also serves to increase the mechanical stability of the matrix and to reduce its rate of resorption by the body. Ideally, the degree of cross-linking should be such that the rate of degradation of the matrix matches the rate of tissue regeneration.

Physically, cross-linking may be carried out by heating, but this must be effected carefully to avoid undesired loss of resorbability. Heating to temperatures of 100-120° C. for a period of from about 30 minutes to about 5 hours is preferable. More preferably, cross-linking may be effected by UV irradiation using a UV lamp, e.g., for a period of up to 8 hours.

As noted above, the collagen matrix material advantageously contains glycosaminoglycans (GAGs). The latter actually reacts with collagen to effect some cross-linking and produces an insoluble product. If necessary, further cross-linking can be effected by heating the material, by UV irradiation, or by further chemical cross-linking as discussed above. The reaction between the glycosaminoglycans and collagen can be effected at ambient temperatures at a pH in the range 2.5-3.5. The material may be subjected to freezing and freeze-drying immediately after such treatment.

For example, GAGs such as chondroitin sulphate (CS) may be covalently attached to the matrix using 1-ethyl-3-(3-dimethyl aminopropyl) carbodiimide (EDC) and N-hydroxysuccinimide (NHS) utilizing known methods. EDC/NHS crosslinking may be utilized for immobilizing GAGs with matrices, which may include dermatan sulphate, heparin, heparan sulphate, and hyaluronic acid, as well as CS as indicated above.

Slurry formation may be effected by raising the pH of a collagen mass. In this procedure, the mass is cooled to about 4° C. and the pH value slowly raised by addition of cold aqueous NaOH at 4° C. up to a pH value about 6.5-7.5. Subsequently, the mass is held at ambient temperature for about 15-25 hours. In this time, the slurry is formed and after slurry formation, the mass can be molded, frozen and freeze-dried.

A still further alternative is to neutralize a collagen mass to a pH value about 6.8-7.4, subsequent to removal of air. The mixture is placed in the mold and incubated for about 15-20 hours at 37° C. A fine slurry develops which can subsequently be frozen and freeze-dried.

After molding the slurry, the material is frozen. In order to obtain a reproducible pore size, the freezing must be carefully controlled and the rate and time of freezing, the pH value and the particle size must be accurately controlled.

The matrix is then freeze-dried and subsequently heated to about 110-130° C. In this way, some cross-linking is effected. Subsequently, the freeze-dried matrix may be adjusted to the required thickness. The matrix is then sterilized, for example by gamma-irradiation or with ethyleneoxide. Sterilization by strong irradiation e.g. with $^{60}$Co in doses of 25 kGy may deactivate the BMPs. In such circumstances, the sterile matrix may be impregnated with BMPs in sterile saline prior to implantation.

The thickness of a matrix in accordance with the present invention may be within the range of about 0.2-2 cm, preferably about 0.3-1.5 cm, more preferably about 0.4-1 cm, and most preferably about 0.5-0.8 cm.

When cross-linking is effected utilizing chemical agents, various aldehydes such as hyaluronate polyaldehyde, formaldehyde or glyoxal may be used. Suitable chemical cross-linking agents include hyaluronate polyaldehyde, hexaethylene di-isocyanate, di-ethyl-3-(3-dimethyl aminopropyl) carbodimide (EDC), and N-hydroxy succinimide (NHS) or a mixture of EDC and NHS.

There exists a wide range of glycosaminoglycans and proteoglycans which have different and sometimes undesirable properties. Thus, although it is possible to incorporate into the matrix glycosaminoglycans from different sources which do not have the same composition, molecular weight and physiological properties as glycosaminoglycans from cartilage, it is particularly preferred to use glycosaminoglycans from cartilage itself.

As noted above, it is desirable to subject a collagen matrix to some degree of cross-linking in order to restrict the extent of swelling when the matrix comes in contact with aqueous fluids, while retaining the ability of the matrix to be resorbed.

Such swelling leads to loss of strength and shape. The matrix according to the invention may advantageously be manufactured by subjecting cartilage tissue to defatting followed by treatment with a base whereby proteoglycans and glycosaminoglycans are removed.

The cartilage material will normally be that from readily available animal sources such as cattle, sheep or pigs. The preferred material is hyaline cartilage from pigs. This contains collagen and glycosaminoglycan in desirable proportions and is available in suitably large quantities.

The cartilage is preferably frozen after slaughter and subjected to size reduction, for example to a particle diameter of about 8 mm. Before size reduction, the cartilage is preferably soaked in water and mechanically separated from flesh, bone and other unwanted materials.

The particulate cartilage is then preferably subjected to dewatering by treatment with a water miscible organic solvent such as acetone, which also serves to remove some fat. The dewatering shrinks the collagen fibres and separates them from each other so that the subsequent defatting step is optimized. The material is then subjected to defatting with a fat-solvent such as a hydrocarbon e.g., hexane, or a halogenated hydrocarbon.

After defatting, the material is thoroughly washed and this is continued until as much water has been taken up as was present originally. By this procedure, the material is optimized for the base-treatment which follows.

The base-treatment may be effected with a strong alkali, for example an alkali metal hydroxide, e.g., sodium hydroxide, for example at a concentration of 1-8% by weight. The treatment time, which will vary according to the raw material and alkali concentration, is generally 10-48 hours. The treatment temperature will generally be below 20° C. The pH value is normally in the range 12-14. The above conditions are those which are optimal for treatment with NaOH. Treatment with other bases may require slightly modified conditions.

The base-treatment has the following effects:

Small quantities of residual fat are saponified. The non-collagen, alkali soluble proteins are denatured, destroyed, dissolved and eliminated.

The amide groups in the collagen are saponified, thereby changing the electric charge and the isoelectric point of the collagen.

Bacteria, prions and viruses are inactivated and the collagen is thus sterilized.

It has been found that by this treatment, proteoglycans undergo a useful modification which can be characterized as follows:

The covalent binding of glycosaminoglycans to the core protein in proteoglycans is cleaved. In this way the glycosaminoglycans can be liberated from the protein of the proteoglycans. This is termed β-elimination.

By the base-treatment, the core protein is split into small peptides which may be removed from the reaction mixture by dialysis or ultra filtration.

Due to the strong negative charge, the glycosaminoglycans form water soluble salts which can partially be washed from the collagen. These are, however, uncleaved or only slightly cleaved by the base-treatment and can be separated from peptides by dialysis. A part of the glycosaminoglycan (about 3% by weight of the collagen) is bound to the collagen.

Purified glycosaminoglycans may be obtained by dialysis or ultrafiltration of the extract arising from the base-treatment step.

According to a procedure of the present invention, enzymatic treatment is, in general, not used, in view of the variety of different substances present. However, further steps include treating the material with an organic or inorganic acid, such as hydrochloric acid. This has the following effect:

Unwanted acid sensitive materials are removed; the fibre structure is loosened.

Subsequently, the material is washed, generally until the pH value of the material is between 2.5 and 4.0. The pH value of the material is preferably controlled accurately. The pH value of the material should be uniform across the cross-section of the cartilage.

After the acid treatment, the cartilage is in a water-swelled condition. The material is then subjected to mechanical size-reduction, for example using a colloid mill. The concentration of the collagen in the aqueous medium is then about 2.5-3.5% by weight. The pH value of this mixture should be somewhat acid, for example 3.5-4.5.

At this point, one or more glycosaminoglycans may be added to the purified collagen mass, for example in the range 0.1-40% preferably 1 to 15%, of the weight of collagen.

The glycosaminoglycans added to the collagen preferably are extracted from the natural cartilage, as indicated above. The matrix will then contain, besides collagen, the glycosaminoglycans hyaluronic acid, chondroitin sulphate and keratan sulphate. The chondroitin sulphate and keratan sulphate are covalently bonded to the core protein while hyaluronic acid is, indeed, bound to the proteoglycan but not covalently.

By the action of the base, the bonding to the core protein is cleaved and the glycosaminoglycan is freed from the protein. Additionally, the core protein is cleaved to small peptides which are readily removed by dialysis or ultrafiltration. It is important that the core protein is removed, since this may be immunologically active. The removal of the core protein is thus an important part of the process of the present invention.

The recovery of the glycosaminoglycans from the base extract may be effected as follows:

The medium is neutralized to a pH value in the range 6-8.

The non-collagen proteins care removed by treatment with an adsorbent such as kaolin.

Ultrafiltration of the liquid is effected, using a membrane which permits the passage of molecules of weight less than 10000 daltons.

Concentration of the liquid is effected to a solids content of about 2-5 weight percent.

After admixture of the glycosaminoglycan with the collagen, the material is homogenized still further in a colloid mill and the solid content is adjusted to 1.5-2.5 weight percent. This mass can then serve for the production of two types of product, namely a sponge or a collagen sheet.

For the production of a sponge, the mass resulting from homogenization is frozen. The freezing must be precisely controlled, whereby the freezing time, pH value and particle size are exactly maintained in order to provide a reproducible pore size. The frozen product is then freeze-dried. After freeze-drying, the sponge is warmed to 120-140° C. for at least 2 hours. In this way, the material is stabilized by light cross-linking. After the freeze-drying the material is cut to a desired thickness, stamped to the required shape, sterilized and packed.

Because the use of sponges is limited for use in some fields due to insufficient strength, the collagen matrix according to the invention can advantageously be used for the production of collagen sheets, which are suitable for use in a wide range of medical indications.

For the production of collagen sheets, the concentration of purified collagen fibres in the liquid suspension should be in the range 0.2-3 weight percent, advantageously 0.5-2 weight percent. Air is preferably removed.

A gel is then formed as an intermediate step. The production of the collagen gel can be effected by various techniques known for gel formation.

The gel is then dried, normally on a plate. In this way, not only is water removed but insoluble collagen-glucosaminoglycan products are formed which are very beneficial for the growth of cells.

As noted above, the matrix for use in accordance with the present invention may comprise a porous bone mineral matrix material or a combination of collagen matrix material and porous bone mineral matrix material. A bone mineral containing matrix material utilized in accordance with the present invention may contain any suitable additions as outlined above with respect to collagen matrix materials in accordance with the present invention.

The purified bone mineral may, for example, be a product as described in International Patent Application WO 86/07265 (PCT/GB86/00310). Such products may be prepared by rigorously de-greasing particulate bone, e.g. bovine femurs, and treating with ammonia or an organic amine to degrade residual protein followed by extensive water washing. Such material remains resorbable on implementation, assisting the remodeling process.

It is also possible to prepare purified bone mineral by calcinating particulate cancellous or cortical bone e.g. at 900 C for 24 hours. Such calcined bone mineral is of use where permanent, non-resorbable implants are required, for example in ridge augmentation.

In either way after removal of organic material, the bone is excessively brittle and its strength is greatly improved by treatment according to the invention.

The present invention is useful for reconstructing bone tissue defects such as in the maxilla, in articulating joints such as the knee, and the spine.

The bone mineral product for use in the present invention may be comprised of particles of porous bone mineral and/or collagen fibers, provides a substrate for osteoblasts and osteocytes to affect bone regeneration.

The collagen of the product of the present invention also imparts strength to the brittle bone mineral.

According to one aspect of the present invention a purified particulate bone mineral product is provided for use in medicine, the particles of said mineral being substantially free from all endogenous organic material and having at least at the surface thereof resorbable, physiologically compatible, collagen material, preferably collagen II material.

Bones from slaughtered animals are an inexpensive raw material available in large quantities. They contain 50 to 60% of very finely crystallized hydroxylapatite bonded by collagenic tissue and containing significant qualities of proteinaceous and other matter as well as associated fat and muscle tissues. In view of its biologically formed crystal structure it can also be considered as a highly biocompatible prosthetic bone replacement. Owing to its large specific surface it can also be used, for example, as an adsorbent or as a support for slow release medication.

Natural bone mineral comprises hydroxyapatite like crystallites with a particular degree of crystallinity, habit and size (irregular plate-like morphology, 5-10 mm in thickness 10-50 mm in length) and surface chemistry resulting from the calcium to phosphate ratio (37.5-38.0% calcium and 15.5-519.0% phosphorus). Also present in the natural bone mineral are small amounts of noncrystalline entities and other calcium phosphate crystalline phase including the minerals Brushite and Nihitlockite, and octa-calcium phosphate. The inorganic phase of bone contains porosity including ultrastructural interstices (10-100 mm) between the crystallites occurring naturally and produced by removal of the organic phase, and microscopic spaces (1-20 microns, including osteocyte lacunae, canaliculi, vascular channels, Volkmann's canals, and the canals of Haversian systems (100-500 mm). The specific surface area, which is a measure of porosity is in the range 50 to 100 m2/gm as determined by mercury Porosimetrv. The crystallinity of bone mineral can he characterized by X-ray diffraction and the porosity and crystallite morphology and size by electron microscopy. Small amounts of nonapatitic crystallites can be detected by thermogravimetric analysis.

However, the composition and structure of natural bone mineral cannot be duplicated by products formed in vitro or by naturally occurring hydroxyapatites prepared previously. Two methods for the purification of natural bone mineral have been proposed, namely calcination and solvent extraction.

The temperature needed during calcination for the incineration of the organic constituents of the bones are rather high. This leads to extensive recrystallization of the mineral part with formation of much coarser crystals. The so formed material exhibits a relatively small specific surface. Thus, such material is not readily remodeled to form new bone on implantation and implants may remain unremodelled indefinitely although this may be acceptable for some purposes.

In the extraction processes the proteins are extracted from degreased bone with a suitable solvent. The resulting bone mineral is then washed to remove the solvent.

In both cases, when organic impurities are removed from the natural bone to leave only the bone mineral, the strength of the material is greatly reduced and the individual pieces of purified bone mineral are consequently extremely brittle. This renders handling of the material difficult and may lead to undesirable effects on implantation.

The bone mineral will normally be in the form of particles of average diameter in the range 0.1 to 10 mm. Particles for incorporation into collagen II fiber will preferably be of spongifosa bone and will generally be in the size range 0.1 to 5 mm, preferably 0.5 to 2 mm. It may be beneficial to the close packing of the bone mineral particles to use a mixture of two or more particle sizes, e.g. 0.25 to 1 mm and 1 to 2 mm or a broad range e.g. 0.25 to 2 mm.

The purified bone mineral may be obtained, for example, by the method described above. Thus, for example, fats may be removed using one or more conventional fat solvents such as ethers, e.g. dimethyl ether; ketones e.g. acetone; or hydrocarbons or halogenated hydrocarbons e.g. heptane or methylcylcohexane or toluene.

It may be advantageous to remove an extractant such as toluene by an intermediate extraction with a water miscible solvent such as ethanol before proceeding further. Collagen material may be dissolved using proteolytic agents such as bases e.g. Potassium hydroxide in glycerol, or organic bases such as amines, e.g. ethylene diamine, or amides such as formamide, preferably at elevated temperatures. Such agents are preferably water-miscible to facilitate removal by water washing. Especially good results have been obtained using bone extracted with refluxing ethylene diamine.

Extraction may advantageously be continued at each stage, if necessary with changes of solvent, until no further material is extracted, e.g. for periods up to one or two weeks. It may be advantageous to comminute further after initial protein removal since the bone is more readily fractured at that stage than before extraction. After treatment with base, excess solvents are rigorously removed e.g. by evaporation and/or, where suitable, water washing.

The material is normally subjected to a drying step. It may be convenient to sterilize the material at this stage, e.g. by heat treatment which may effect further purification.

Commonly owned U.S. Pat. No. 5,573,771 (incorporated herein by reference) discloses a medicinal bone mineral product in which the bone mineral is strengthened by a matrix made up of Type I collagen (collagen I), or a mixture of Type I collagen and Type III collagen (collagen I and collagen III).

Collagen occurs in a number of forms in the animal body, and different tissues contain different proportions of the respective types. Collagen sponge material used in medicine and in cosmetics is generally derived from skin and tendons, and is comprised predominantly of collagen I and/or collagen III. Bone collagen comprises predominantly collagen I and collagen III.

Collagen II material may include, in addition to substantially pure collagen II, various proportions of collagen I, collagen III and mixtures thereof blended with the collagen II. For example, the collagen II material may have mixed therein about 0.1-10% by weight (preferably about 0.1-5% by weight) collagen III, and/or about 1-50% by weight collagen I.

Collagen II material may impregnate each of the individual particles to improve the handling properties of the product in manufacture and use. In that case, the weight ratio of the collagen II material to the purified bone mineral is advantageously greater than 1:40, preferably greater than 1:8 and less than 4:1, preferably less than 1:2. Advantageously, the collagen II material comprises about 1-30% by weight of the bone mineral product of the present invention, preferably about 5-15% thereof. The collagen II material penetrates the porous structure of the bone mineral and effectively replaces some of the natural proteinaceous material previously present in natural bone which, although providing strength, also gives immunological tissue reactions on implantation of the bone mineral.

The collagen II material may be used to provide a matrix for the particulate bone mineral from which shaped articles may be formed. In this case, it is possible to use Collagen II together with a gel forming macromolecular substance such as gelatin. The weight ratio of the fibrous material to the bone mineral may, for example, be in the range 1:40 to 3:20 e.g. about 1:10. The gel phase advantageously amounts to 2 to 20% by weight of the bone mineral, e.g. about 5%. Where gelatin is used as the gel phase, it may be lightly cross-linked, e.g. with about 0.28 formaldehyde.

The bone mineral preferably is from spongifosa bone, and is linked with the collagen II fibers to add physical strength to the matrix. In preferred embodiments, the bone mineral/collagen product according to the present invention is used as a matrix to regenerate cartilage defects in articulating joints where additionally bone loss is present.

The bone mineral product according to the invention may be used for bone regeneration in maxilla, knees, feet, spine, etc., and as a remodeling implant or prosthetic bone replacement, for example in orthopedic surgery including hip revisions, replacement of bone loss, e.g. in traumatology, remodeling in maxillo-facial surgery or filling periodontal defects and tooth extraction sockets, including ridge augmentation. The impregnated particulate material of the invention may thus be used for packing into a variety of bone cavities and its reduced brittleness is significant in aiding the handling and packing procedure.

The invention is applicable to repair of maxilla bone defects, and regeneration of articular joint defects in which both the cartilage and underlying bone is damaged. The bone mineral/collagen product of the invention can be utilized to fill in an area of bone damage, and the filled-in area of bone defect then can be covered with a collagen membrane.

To enhance regeneration, extracellular cultivated osteoblasts or osteoblast-forming stem cells can be added to the bone mineral/collagen matrix of the invention before implantation, and the charged matrix then can be implanted during open surgery or arthroscopic surgery. Alternatively, or in addition thereto, the implanted matrix can be covered with a collagen membrane comprised of collagen I, II and/or III, or covered by a synthetic membrane. Such collagen membrane or synthetic membrane can alternatively or additionally be charged with extracellular cultivated osteoblasts or osteoblast-forming stem cells, with the membrane being applied over the filled-in bone implant by open surgery or arthroscopic surgery.

Where the bone is to be used as a drug carrier, as indicated in the above International Patent Application the bone mineral may usefully carry one or more absorbed drugs or other physiologically active substances. In accordance with one embodiment, the product of the invention comprises at least one absorbed pharmaceutically or biologically active substance or mesenchymal stem cells having an ability to differentiate into cells to regenerate cartilage and/or bone.

Physiologically active substances which may be adsorbed onto the bone mineral are preferably at least partially water-soluble and include antibacterial substances such as antibiotics e.g. penicillins, cephalosporin, aminoglycosides etc., sulfonamides and, in particular, condensation products of formaldehyde with taurinamide or N-substituted taurinamide. The latter compounds may be represented by the formula

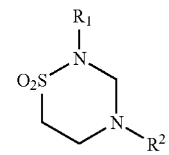

where R1 is hydrogen or a C1-4 alkyl group and $R^2$ is hydrogen or a group of the formula

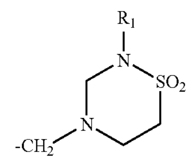

wherein $R^1$ has the above meaning.

The compound of formula (I) in which $R^1$ and $R^2$ are both hydrogen is taurultam while the compound in which $R^1$ is hydrogen and $R^2$ has the formula (II) is taurolidine. These compounds act as methylol transfer agents and are effective not only in destroying both gram negative and gram positive bacteria but also in inactivating both endotoxins and exotoxins produced by the bacteria.

Other useful physiologically active substances include proteins and polypeptides capable of assisting bone regeneration especially non-collagenous proteins derived from bone matrix and bone cells. These include mitogenic factors such as skeletal growth factor and morphogenic and angiogenic factors as well as transforming bone growth factor. Growth factors from the matrix such as ossein or more preferably osteopoietin are particularly beneficial.

According to one embodiment, a pharmaceutically active substance is selected from the group consisting of bone morphogenic proteins (BMPs) such as BMP-2-8, or other skeletal matrix molecules, as well as signaling peptides such as transforming growth factor-β, TGF-β, TGF-β1, vascular endothelial growth factor (VEGF), insulin-like growth factor (IGF), parathyroid hormone related protein (PTHrP) and platelet derived growth factor (PDGF).

It will be appreciated that physiologically active substances may alternatively or additionally be incorporated in the macromolecular substance e.g. impregnated gelatin. This is particularly suitable for proteins such as the bone growth factors set out above.

Absorption and/or adsorption of the physiologically active substance is preferably effected by immersing the treated bone mineral in an aqueous solution thereof preferable under sterile conditions. The concentration of the active substance is preferably relatively high to facilitate adsorption and/or absorption and will depend in part on the solubility of the active material.

For any of the above products, the matrix according to the invention can be supplemented with active substances. Thus any physiologically active substance which is water soluble or water dispersible can be used. Thus, the matrix may advantageously contain medicinal substances such as antibacterials, e.g., taurolidine, taurultam, or antibiotics such as tetracyclines and gentamycins.

A method in accordance with one embodiment of the invention comprises exposing a bone defect in the maxilla or other skeletal defect, inserting a charged matrix which has been sized to fit the area of damaged bone, and fixing the sized matrix in the area of damaged bone by any suitable means such as adhesive or suturing the matrix over the bone defect.

The following examples are given by way of illustration only.

Example 1

Frozen cartilage from freshly slaughtered pigs was steeped in cold water, thoroughly washed through and mechanically purified from flesh residues, bones and hard pieces. Subsequently, the material was washed for 30 minutes under flowing water.

Subsequently, the material was ground three times in a homogenizer. The optical particle size at the end of size reduction was about 8 mm.

The cartilage pieces were dewatered by washing 4 times with acetone, each time for 8 hours. The cartilage was then defatted by extraction 4 times with n-hexane. Each treatment lasted at least 8 hours. The ratio of hexane to cartilage was 1:10.

After defatting, the cartilage was swelled in drinking water. The ratio of water:material was 10:1. The treatment time was 24 hours.

The material was then treated with NaOH (5% by weight) whereby the ratio of cartilage to liquid was 1:4 and the treatment time was 32 hours. During the treatment, the pieces of cartilage were well stirred. Subsequently, the alkali was washed from the cartilage. The original pH of 14 was thereby reduced to 9-11. The dissolved impurities were washed out and separated from the cartilage. The liquid resulting from the alkaline treatment was collected for the recovery of glycosaminoglycan.

The collagen material was then treated with strong HCl (about 3% by weight) initially at a pH value under 1.0. The treatment time was 4-6 hours.

Subsequently, the material was washed with cold water long enough for the pH value to rise to 3-3.5.

All impurities were removed and the product was a salt-free collagen mass, suitable for-production of a sponge or other collagen material. For that purpose, the cartilage mass may be, according to the intended result, degassed, frozen and freeze-dried.

Example 2

The extract resulting from alkaline treatment in Example 1 contained glycosaminoglycan, alkali, denatured proteins and salts. The extract was firstly neutralized with HCl, the pH value after neutralization being 6. The extract was then treated with a filter aid, namely kieselguhr, which had the effect of removing the denatured proteins. 0.5 weight percent of kieselguhr was introduced into the extract and removed by filtration together with the denatured protein.

The supernatant was then submitted to ultrafiltration using a membrane having a molecular weight cut off at about 10000 daltons. In this way, salts were removed to leave purified glycosaminoglycan.

The glycosaminoglycan solution so obtained was admixed with collagen material from above to provide a collagen II matrix containing glycosaminoglycan.

Example 3

(1) Determination of Hexosamine and Amino Acid Residues in Collagen Sponges and Fleeces Each sample, exactly weighed (about 10 mg) was hydrolyzed in 10 ml of 3M or 6M HCl at 1.05° C. for 15 or 20 hours under purified nitrogen in a sealed tube. After cooling the tube in a refrigerator and opening the tube, the contents were transferred to a 25 ml long neck flask and dried at 40° C. in a vacuum-rotation dryer (Rotavapor RE120, Büchi, Switzerland) under water jet vacuum. After dissolving the residue in 5 ml water, the residue was again dried under water jet vacuum. Subsequently, the residue was taken up in 5 ml loading buffer (0.2M relative to Na+) at pH 2.2. For determination of the glucosamine and galactosamine values, after previous dilution of an aliquot with loading buffer (1+10) 150 μl of the sample hydrolyzed in 3M HCl was injected into the cartouche of an amino acid analyzer (AlphaPlus, type 4151, Pharmacia-LKB, Freiburg) and evaluated by comparison with a standard with the help of a computer (Shimadzu, Duesseldorf). The same procedure was effected with the sample hydrolyzed in 6M HCl, wherein 50 μl were injected in a further test cartouche. The double hydrolysis in 3M and 6M HCl is necessary for optimization of the hexosamine and amino acid analysis since the maximal values for hexosamine and also tyrosine are only obtained after hydrolysis in 3M HCl while maximal values are only obtained for valine, isoleucine and leucine after hydrolysis in 6M HCl.

(2) Determination of Native Collagen Content in Collagen Sponges and Fleeces 25-30 mg (exactly weighed out) of sample were introduced into 30 ml 0.1M sodium hydrogen carbonate solution (pA, Merck, Darmstadt) pH 8.2 to which 1.5 ml of a 6 mg/ml trypsin solution (lyophilized preparation from bovine pancreas, Boehringer, Mannheim) and incubated for 8 hours at 23±1° C. in a shaking water bath (Julabo SWI, Seelbach). After cooling the sample in a cold room to 4° C., it was centrifuged at 4° C. in a 60 Ti-Rotor (Beckman, Munich) at 32000 RpM for 30 minutes. The residue was filtered in a stirred ultra filtration cell (Mod 8010, Amicon, Witten) through a Diaflow-Filter PM 10 (Amicon, Witten) of diameter 25 mm and 1 ml of the filtrate was hydrolyzed in 6M HCl for 20 hours at 105° C. The further working up and analysis of the hydrolysate is identical with that described under (1) above with the exception that the further uptake of the sample after twice evaporating to dryness, was in 150 μl loading buffer, whereby 150 μl was injected into the test cartouche of the amino acid analyzer. The hydroxyproline value obtained after the amino acid analysis (in μmol/g starting substance), represents the part of the degradable collagen in the sample. When the hydroxyproline value of a parallel hydrolysis (6M HCl and analyzed sample (see (1) above) which represents the total collagen content, is compared with the hydroxyproline value, the percentage proportion of the "native", that is trypsin non-degradable collagen is indicated.

The results are shown in the following table.

TABLE

| | μmol/g | mol/1000 mol |
|---|---|---|
| Hydroxyproline | 795.4 | 97 |
| Aspartic acid | 381.7 | 47 |
| Threonine | 190.1 | 23 |
| Serine | 257.0 | 31 |
| Glutamic acid | 691.3 | 84 |
| Proline | 913.2 | 112 |
| Glycine | 2614.6 | 320 |
| Alanine | 864.9 | 106 |
| Cysteine/2 | 11.5 | 2 |
| Valine | 195.7 | 24 |
| Methionine | 62.7 | 8 |
| Isoleucine | 92.8 | 11 |
| Leucine | 229.9 | 28 |
| Tyrosine | 27.0 | 3 |
| Phenylalanine | 119.9 | 15 |
| Histidine | 39.8 | 5 |
| Hydroxylysine | 126.4 | 15 |
| Lysine | 173.5 | 21 |
| Arginine | 395.5 | 48 |
| Total | 8182.9 | 1000 |
| Glucosamine | 9.68 | 1.18 |
| Galactosamine | 46.30 | 5.66 |
| Total Hydroxyproline | 795.4 μmol/g | |
| Trypsin-degradable hydroxyproline | 36.9 μmol/g | |
| "Native" collagen content | 95.4% | |

Example 4

Bovine femur bones were boiled in hot water until clean, comminuted to a particle size of 5 to 10 mm. and extracted under reflux with toluene for 24 hours in a Sohxlet apparatus. The material was further extracted with ethanol to remove toluene and then extracted at elevated temperature with an azeotropic mixture of ethylene diamine and water (85:15) for 8 days, with several changes of solvent until substantially no further organic material was extracted. The product was then air dried at 100° C.

The dried product was further comminuted to an average particle size of 0.2 to 2 mm and sterilized in the autoclave. Pieces of bovine femur spongifosa bone, typical diameter 10 mm, were purified by the same technique, omitting the final granulation.

Example 5

Frozen cartilage from freshly slaughtered pigs was steeped in cold water, thoroughly washed through and mechanically purified from flesh residues, bones and hard pieces. Subsequently, the material was washed for 30 minutes under flowing water.

Subsequently, the material was ground three times in a homogenizer. The optical particle size at the end of size reduction was about 8 mm.

The cartilage pieces were dewatered by washing 4 times with acetone, each time for 8 hours. The cartilage was then defatted by extraction 4 times with n-hexane. Each treatment lasted at least 8 hours. The ratio of hexane to cartilage was 1:10.

After defatting, the cartilage was swelled in drinking water. The ratio of water:material was 10:1. The treatment time was 24 hours.

The material was then treated with NaOH (5% by weight) whereby the ratio of cartilage to liquid was 1:4 and the treatment time was 32 hours. During the treatment, the pieces of cartilage were well stirred. Subsequently, the alkali was washed from the cartilage. The original pH of 14 was thereby reduced to 9-11. The dissolved impurities were washed out and separated from the cartilage. The liquid resulting from the alkaline treatment was collected for the recover of glycosaminoglycan.

The collagen material was then treated with strong HCL (about 3% by weight) initially at a pH value under 1.0. The treatment time was 4-6 hours.

Subsequently, the material was washed with cold water long enough for the pH value to rise to 3-3.5. All impurities were removed and the product was a salt-free collagen mass, suitable for production of a sponge or other collagen material. For that purpose, the cartilage mass may be, according to the intended result degassed, frozen and freeze-dried.

Example 6

The extract resulting from alkaline treatment in Example 5 contained glycosaminoglycan, alkali, denatured proteins and salts. The extract was firstly neutralized with HCl, the pH value after neutralization being 6. The extract was then treated with a filter aid, namely kieselguhr, which had the effect of removing the denatured proteins. 0.5 weight percent of kieselguhr was introduced into the extract and removed by filtration together with the denatured protein.

The supernatant was then submitted to ultrafiltration using a membrane having a molecular weight cut off at about 10000 Daltons. In this way, salts were removed to leave purified glycosaminoglycan.

The glycosaminoglycan solution so obtained was admixed with collagen material from above to provide a collagen II matrix containing glycosaminoglycan.

Example 7

2.0 g of collagen II material from Example 6 is comminuted with 500 g distilled water in a blender. This dispersion is centrifuged and the supernatant water removed. To the resulting collagen fiber slurry is added 17.5 g of granulated cortical bovine bone purified by the above procedure of Example 1, followed by thorough mixing and removal of water by suction (70 mm). The granulated bone has a particle size 0.5 to 1.0 mm. After removal of water, 5 mls of a 9% w/w aqueous gelatin solution are added (cross-linked with 0.6% of 35% aqueous formaldehyde) and the mixture again suction dried.

The sponge mass is cut into pieces and dried in vacuo at 60° C. The pieces of sponge are packed into polyethylene containers and sterilized by gamma irradiation.

Example 8

Matrices produced in accordance with Examples 1, 2, 3, 4 and 7 are charged with a suspension of osteocytes, osteoblasts, stromal stem cells in bone marrow or osteoblast-forming stem cells to form a bone healing combination material in accordance with the present invention.

Osteoblasts are cultivated from autologous sources, grown in an external laboratory, charged to the matrix, and then transplanted to the defect, e.g., periodontal and/or bone loss in the maxilla, or general skeletal defects. The transplant site then is covered with a collagen membrane, which may have a barrier function such as Biogide® referred to above.

The invention claimed is:

1. A bone healing material comprising a matrix carrying cultivated bone-forming cells selected from the group consisting of osteocytes, osteoblasts, stromal stem cells and stem cells committed to differentiation into bone-forming osteoblasts, wherein said matrix is selected from a group consisting of (1) a membrane which comprises a sheet of a purified collagen material derived from natural collagen-containing tissue, said membrane comprising a barrier layer including an outer smooth barrier face to inhibit passage of cells therethrough and further including a fibrous face opposite said smooth barrier face, said membrane comprising collagen I, collagen III or a mixture of collagen I and collagen III; (2) a collagen II sheet comprising collagen II having an open texture; and (3) a multi-layer collagen sheet comprising said membrane and said collagen II sheet wherein said collagen II sheet is adhered to said fibrous face of said membrane.

2. The material of claim 1 wherein said stromal stem cells are present in bone marrow, and said matrix carries said bone marrow.

3. The material of claim 1 wherein said matrix comprises said multi-layer collagen sheet.

4. The material of claim 1 wherein said matrix comprises said membrane comprising collagen I, collagen III or a mixture thereof.

5. The material of claim 1 wherein said matrix comprises said collagen II sheet.

6. The material of claim 1 wherein said matrix comprises said membrane comprising collagen I, III or said mixture thereof; said collagen II sheet; or multi-layer collagen sheet.

7. A method of utilizing the material of claim 1 for reconstructing bone tissue, comprising contacting a bone loss defect with the material of claim 1 so as to promote reconstruction of bone tissue at said defect.

8. The method of claim 7 wherein said stromal stem cells are present in bone marrow, and said matrix carries said bone marrow.

9. The method of claim 7 wherein said matrix comprises said membrane comprising collagen I, collagen III or a mixture thereof.

10. The method of claim 7 wherein said matrix comprises said collagen II sheet.

11. The method of claim 7 wherein said matrix comprises said multi-layer collagen sheet.

* * * * *